United States Patent [19]

Mizushima et al.

[11] Patent Number: 5,565,444
[45] Date of Patent: Oct. 15, 1996

[54] OSTEOGENESIS PROMOTER AND OSTEOPOROSIS REMEDY

[75] Inventors: Yutaka Mizushima; Yasuo Suzuki, both of Tokyo, Japan

[73] Assignee: LTT Institute Co., Ltd., Kawasaki, Japan

[21] Appl. No.: 537,743

[22] PCT Filed: May 18, 1994

[86] PCT No.: PCT/JP94/00798

§ 371 Date: Nov. 13, 1995

§ 102(e) Date: Nov. 13, 1995

[87] PCT Pub. No.: WO94/26768

PCT Pub. Date: Nov. 24, 1994

[30] Foreign Application Priority Data

May 18, 1993 [JP] Japan .................. 5-149693

[51] Int. Cl.⁶ .................................................. A61K 31/56
[52] U.S. Cl. ................................................................ 514/178
[58] Field of Search ............................................... 514/178

[56] References Cited

U.S. PATENT DOCUMENTS

| | | | |
|---|---|---|---|
| 3,741,990 | 6/1973 | Nelson | 514/171 |
| 5,183,815 | 2/1993 | Saari et al. | 514/172 |

OTHER PUBLICATIONS

Derwent abstract of NL 6407296. 1964.

*Primary Examiner*—Raymond Henley, III
*Attorney, Agent, or Firm*—Oblon, Spivak, McClelland, Maier & Neustadt, P.C.

[57] ABSTRACT

An osteogenesis promoter and/or osteoporosis remedy comprising, as an active ingredient, an androgen derivative represented by the following formula (1):

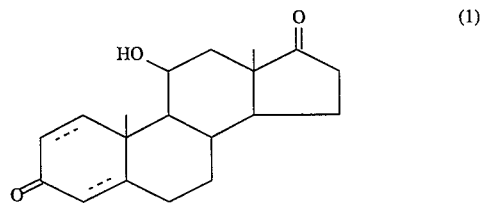

wherein each broken line indicates that the relevant carbon-to-carbon bond is a single bond or a double bond or a salt thereof. The compound (1) activates osteoblasts, promotes osteogenesis and increases the bone mass, so that it is used for the treatment of a morbid condition of lowered osteogenesis due to aging, immobilization, administration of glucocorticoids and so forth. Further, it can increase the bone mass by its osteogenesis promoting effect so that it is useful for the treatment of osteoporosis accompanying the above morbid condition or occurring after ovariectomy or menopause.

6 Claims, 9 Drawing Sheets

OSTEOGENESIS PROMOTER AND OSTEOPOROSIS REMEDY

This application is a 371 of PCT/JP94/00798 filed May 18, 1994.

TECHNICAL FIELD

The present invention relates to a novel osteogenesis promoter and also to an osteoporosis remedy.

Background Art

In recent years, the incidence of osteoporosis has shown a drastic increase keeping step with the aging of population and accordingly, fractures of the femoral neck or the like caused by osteoporosis have increased, posing an increasing threat to our health.

Osteoporosis is a condition in which the bone mass decreases while the components of the bone are kept normal, and is distinguished from a normal phenomenon of aging. What is troublesome is, however, that when osteoporosis advances to a certain extent or further, it becomes difficult for the patient to support his or her own weight, developing problems such as lower back pains, the vertebral column deformation and moreover, susceptibility to fractures at various body parts by light impact.

The condition called "osteoporosis" refers to a condition or syndrome caused by various causes and appears as one of symptoms of various diseases.

It is said that particularly, women tend to suffer from osteoporosis because a drastic decrease occurs in their bone quantities after menopause. Specifically, osteoporosis is considered to be induced by the deficiency of estrogen.

Bones protect the human body from external force and support the body as fulcrums for muscles, so that they are always exposed to physical forces such as pressure, tension and the like. To bear such physical forces is the significance of the existence of bones. It is accordingly presumed that without such physical stimuli, bones lose even their strength in addition to a drastic decrease in mass, resulting in the occurrence of osteoporosis. In short, a reduction in the bone mass is caused when physical stimuli to bones are lost. Osteoporosis characterized by such a cause is called immobilized osteoporosis.

Osteoporosis is, on the other hand, considered to be a representation of calcium dysbolism as one aspect of aging phenomena. Bones amount to 99% of the calcium in the whole body, which means that a decrease in the bone mass leads to a decrease in the calcium of the whole body. The continued deficiency of calcium with aging exasperates the secretion of parathyroid hormones, reduces the bone mass owing to an advance in the bone resorption and causes deposition of bone-released calcium in soft tissues, especially, in blood vessels and the cerebrum, which in turn induces osteoporosis, hypertension, arteriosclerosis, or senile dementia. Osteoporosis is therefore not only a disease of bones but also a representation of aging of the human body and of calcium dysbolism accompanied therewith and is also said to be an index showing in vivo abnormal calcium distribution.

Accordingly, the importance of osteoporosis lies in that because it becomes an index of various diseases of old age and represents the extent of calcium deficiency, the prevention of osteoporosis and the normalization of calcium metabolism conversely lead to the prevention of aging and also diseases of old age.

Examples of osteoporosis remedies clinically used now include calcium preparations, vitamin D derivatives, calcitonin, ipriflavone and the like. These preparations have as their principal effect the control of bone resorption. For postmenopausal osteoporosis, estrogen preparations are administered. Their effect is based on the acting mechanism of controlling an exasperation in bone resorption which is accompanied with a high bone turnover.

In senile osteoporosis, immobilized osteoporosis and glucocorticoid-induced osteoporosis, on the other hand, lowered bone formation is a serious morbid condition. In Europe and America, sodium fluoride was administered as an osteogenesis promoter for such lowered bone formation. It has, however, many adverse effects and therefore is not be used frequently these days.

An anabolic steroid was once used for osteoporosis in view of the report that it promotes bone formation. The above steroid, however, has adverse effects such as virilizing effect and in addition, its effect itself against osteoporosis is not clear so that it is not used clinically at present.

It is only estrogen that has proven to have an evident curative effect for a decrease in the bone mass of an ovariectomized animal. However, estrogen is effective only for postmenopausal osteoporosis and moreover, it has serious adverse effects such as metorrhagia, the occurrence of breast and uterine cancers, and the like. It is the present situation that there are no osteoporosis remedy which is relatively free from adverse effects and is capable of promoting bone formation and increasing the bone mass. There is a report that among in vivo endogenous steroids, dihydroepiandrosterone (DHEA) has a bone-mass improving effect, but its effects on ovariectomized animals are extremely weak.

Calcium preparations, vitamin D derivatives, calcitonin, ipriflavone or the like which are used now as osteoporosis remedies have difficulty in restoring the lost bone mass itself and at the best, may prevent a bone mass reduction, because prevention of bone resorption is considered to be their main effect. On the other hand, combined use of osteogenesis-promoting sodium fluoride and an anabolic steroid has been reported to increase the bone mass. These chemicals however involve so many side effects that they can hardly be used.

There is accordingly a desire for the development of a chemical capable of promoting the formation itself of a bone without substantial adverse effects.

An object of the present invention is, therefore, to provide an osteoporosis remedy which has osteogenesis promoting and bone-mass increasing effects with extremely minimized adverse effects such as virilization.

DISCLOSURE OF THE INVENTION

The present inventors have carried out an extensive investigation toward such an effective osteoporosis remedy. It has been found that an androgen derivative represented by the below-described formula (1) or a salt thereof has osteogenesis promoting and bone-mass increasing effects, is highly safe and is useful as an osteoporosis remedy, leading to the completion of the present invention.

The present invention therefore relates to an osteogenesis promoter and/or an osteoporosis remedy comprising, as an active ingredient, an androgen derivative represented by the following formula (1):

(1)

wherein each broken line indicates that the relevant carbon-to-carbon bond is a single bond or a double bond; or a salt thereof.

The present invention also relates to a method of remedial treatment for osteodysbolism and/or osteoporosis, which comprises administering, to a patient suffering from osteodysbolism and/or osteoporosis, an effective amount of an androgen derivative represented by the above formula (1) or a salt thereof.

The present invention further relates to use of an androgen derivative represented by the above formula (1) or a salt thereof for the promotion of osteogenesis and/or for the remedial treatment of osteoporosis.

The present invention still further relates to an osteogenesis promoter and/or osteoporosis remedy composition comprising an androgen derivative represented by the above formula (1) or a salt thereof; and a pharmaceutical vehicle.

In the osteogenesis promoter and osteoporosis remedy provided by the present invention, the androgen derivative or a salt thereof, as their active ingredient, activates osteoblasts, promotes osteogenesis and increases the bone mass so that it is used for the treatment of a morbid condition of lowered osteogenesis due to aging, immobilization, administration of glucocorticoids and so forth. Further, it can increase the bone mass by their osteogenesis promoting effect so that they are useful for the treatment of osteoporosis accompanying the above morbid condition or occurring after ovariectomy or menopause.

BRIEF DESCRIPTION OF THE DRAWINGS

FIG. illustrates effects of invention compounds on alkaline phosphatase activity of osteoblasts.

BEST MODES FOR CARRYING OUT THE INVENTION

The androgen derivatives (1) useful as active ingredients in remedies according to the present invention include, depending on the presence or absence of bonds indicated by broken lines, four kinds of compounds, which are 11β-hydroxyandrostane-3,17-dione, 11β-hydroxy-1-androstene-3,17-dione, 11β-hydroxy-4-androstene-3,17-dione and 11β-hydroxy-1,4-androstadiene-3,17-dione. Among them, particularly preferred are 11β-hydroxy-4-androstene-3,17-dione (hereinafter abbreviated as "11β-OH-$\Delta^4$-A") and 11β-hydroxy-1,4-androstadiene-3,17-dione (hereinafter abbreviated as "11β-OH-$\Delta^{1,4}$-A") In the present invention, accordingly, an osteogenesis promoter containing 11β-OH-$\Delta^4$-A or 11β-OH-$\Delta^{1,4}$-A as an active ingredient and an osteoporosis remedy containing 11β-OH-$\Delta^4$-A or 11β-OH-$\Delta^{1,4}$-A as an active ingredient are especially preferred.

There is no particular limitation on the salts of these androgen derivatives (1) insofar as they are pharmaceutically acceptable and are formed at the 11-hydroxyl group. The androgen derivative (1) or the salt thereof can each be prepared from androstenedione (4-androstene-3,17-dione) with an aid of 11β-hydroxylating vivo. It can also be formed by cutting the 17-side chain of cortisol, one of glucocorticoids. Chemical synthesis can also be employed for the preparation. Concerning 11β-OH-$\Delta^{1,4}$-A, there is a description in J. Steroid Biochem. Mol. Biol. 40, 731–733(1991) that in the case of a patient (woman) suffering from osteoporosis, its average concentration in blood was 1.75 ng/m while in the case of a normal woman, the concentration was 2.20 ng/m.

In that literature, however, there is no description whatsoever about whether 11β-OH-$\Delta^4$-A has osteogenesis promoting effects or bone-mass increasing effects.

The androgen derivatives (1) and salts thereof (hereinafter called "invention compounds") each of which is an active ingredient in the present invention promote differentiation and proliferation of osteoblasts, enhance bone osteogenesis, and increase the bone mass, thereby improving osteoporosis symptoms. In addition, it has been proved that their sex hormone action is extremely weak.

The followings are the results of tests of the invention compounds on bone metabolism improving effects, osteoporosis improving effects, sex hormone action, protein assimilating effects and estrogenic action.

TEST 1

Effects on the Number of Osteogenic Precursor Cells in Bone Marrow

After the invention compound was administered to a 7-weeks old Wistar or Lewis rat intraperitoneally (Experiment 1) or dorsi-subcutaneously (Experiment 2) for 7 successive days, the femurs and tibias were excised. Marrow cells were collected from the bones so obtained, followed by incubation in a 25-cm$^2$ culture flask for 7 days. For the incubation, the αMEM medium containing 15% fetal calf serum was used. Subsequent to giemsa or alkaline phosphatase staining, the number of fibroblast colony forming units on the culture flask was counted. The number of the fibroblast colony forming units (=FCFUs) is known to correlate with the in vitro ostogenesis. The total number of FCFUs and the number of FCFUs positive to alkaline phosphatase are shown in Table 1 and Table 2, respectively. Experiment 1:

TABLE 1

Influence of the intraperitoneal administration of
the invention compound at 1 mg/kg for 7 successive
days on the formation of FCFUs:
The number of FCFUs (after 7 days) (Wistar rat N = 4)

|  | The total FCFU number | The number of FCFUs positive for alkaline phosphatase |
|---|---|---|
| Control | 36 ± 7 | 7 ± 2 |
| 11β-OH-$\Delta^4$-A | 160 ± 35 | 40 ± 11 |

Experiment 2:

TABLE 2

Influence of the subcutaneous administration of
the invention compounds and testosterone for 7
successive days on the formation of FCFUs:
The number of FCFUs (after 7 days) (Lewis rat N = 4)

|  | The total FCFU number | The number of FCFUs positive for alkaline phosphatase |
|---|---|---|
| Control | 111 ± 48 | 25 ± 11 |
| 11β-OH-$\Delta^4$-A (0.1 mg/kg) | 180 ± 9 | 96 ± 16 |
| 11β-OH-$\Delta^4$-A (1 mg/kg) | 189 ± 26 | 128 ± 19 |
| 11β-OH-$\Delta^{1,4}$-A (0.1 mg/kg) | 178 ± 20 | 85 ± 11 |
| 11β-OH-$\Delta^{1,4}$-A (1 mg/kg) | 217 ± 22 | 117 ± 12 |
| Testosterone (1 mg/kg) | 149 ± 5 | 62 ± 5 |

From the above test results, the invention compounds are considered to exhibit ostogenesis promoting effects by significantly increasing the number of osteogenic precursor cells in the bone marrow. Their effects were potent compared with those of testosterone, an androgenic hormone.

TEST 2

Effects on Serum Osteocalcin

A 7-weeks old Wistar rat was intraperitoneally administered at 0.1 mg/kg with 11β-OH-$\Delta^4$-A for 7 successive days and the concentration of osteocalcin in the serum was measured by radioimmunoassay. The results are shown in Table 3.

TABLE 3

|  | Serum osteocalcin concentration (ng/ml) |
|---|---|
| Control | 67.5 ± 0.8 |
| 11β-OH-$\Delta^4$-A |  |
| 0.1 mg/kg | 72.6 ± 2.7 |
| 5 mg/kg | 75.5 ± 1.0 |

From the above results, the successive administration of 11β-OH-$\Delta^4$-A has been recognized to increase the concentration of osteocalcin, thereby suggesting the promotion of osteogenesis.

TEST 3

Effects of Established Mouse Osteoblasts,
MC3T3-E1, on Alkaline Phosphatase Activity In a 24-well culture plate, the established mouse-calvaria-derived osteoblasts, MC3T3-E1 were incubated for 2 days with the αMEM medium containing 5% fetal calf serum. When the osteoblasts became semi-confluent, the medium was replaced by a medium containing 1% fetal calf serum, followed by incubation for additional 3 days. The medium was then replaced by the αMEM medium (serum-free medium) containing 0.1% bovine serum albumin, followed by incubation for one day. The test compound was then added to the incubated medium and incubation was conducted for further 2 days. Cells were scraped from the medium and then disrupted by a sonicater, followed by the measurement of alkaline phosphatase activity of the disrupted solution. Described specifically, the alkaline phosphatase activity was measured by reacting a substrate (a buffer containing disodium p-nitrophenyl phosphate in 2-amino-2-methyl-1-propanol) and the disrupted solution for 30 minutes and then comparing the absorbance with that of a p-nitrophenol standard solution.

Figure 1:
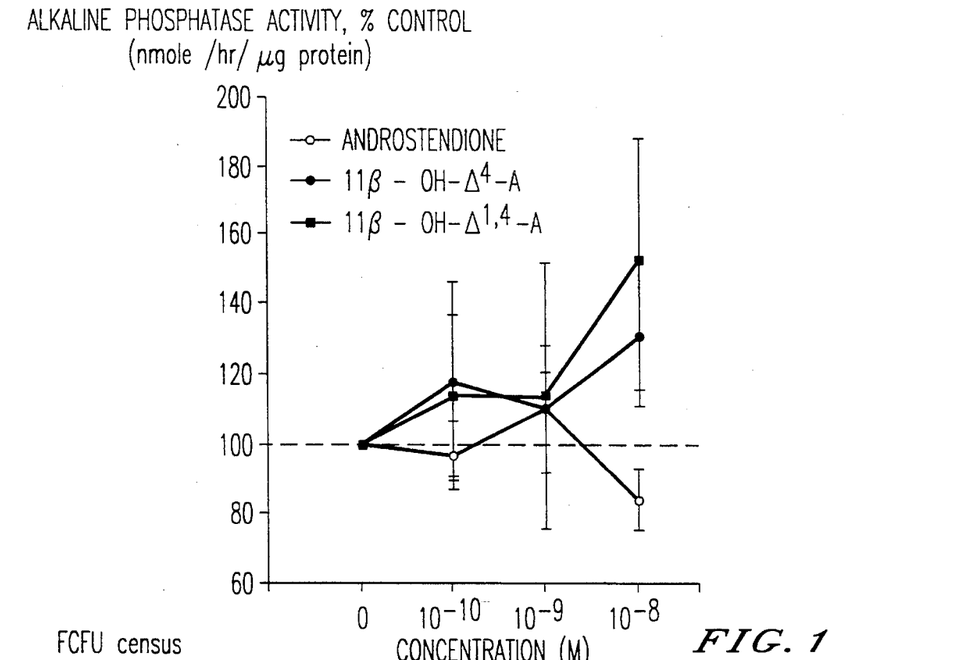

As the test compound, 11β-OH-$\Delta^4$-A and 11β-OH-$\Delta^{1,4}$-A were separately used, while as a comparative compound, androstendione was employed. The results are shown in FIG. 1.

From the results, the invention compounds have been found to have osteogenesis promoting effects as they exasperated the alkaline phosphatase activity of osteoblasts and showed osteoblast activating effects.

TEST 4

Figure 2:
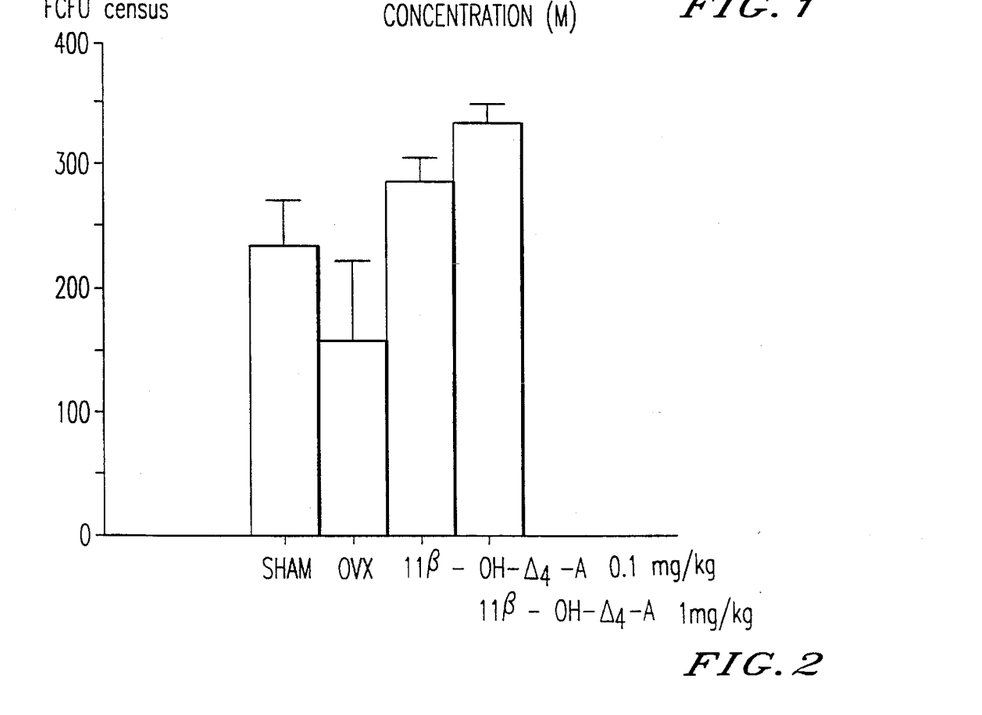
FIG. 2 illustrates effects of the invention compounds on the FCFU forming ability after ovariectomy.
Figure 3:
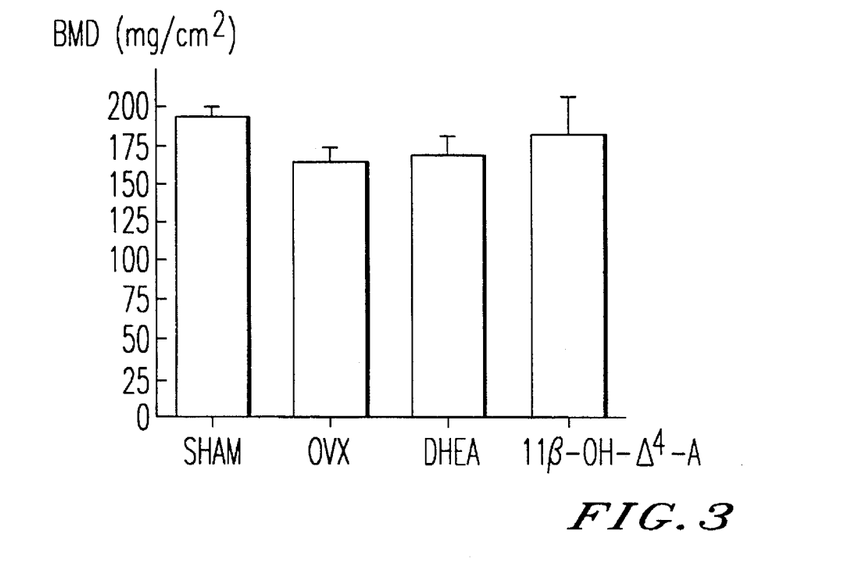
FIGS. 3–6 illustrate bone-mineral increasing effects of the invention compound at the femoral proximoepiphysis, the femoral diaphysis, the femoral distoepiphysis and the whole femur, respectively.
Figure 4:
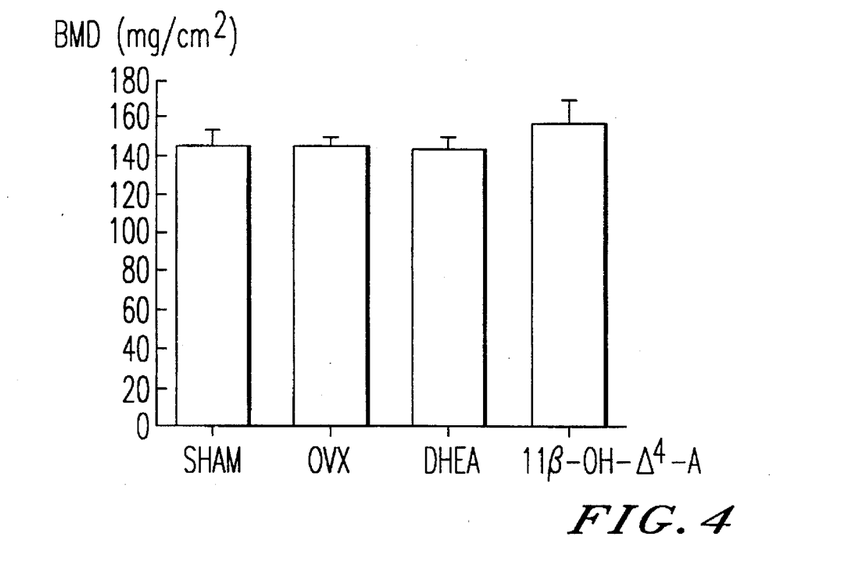
Figure 5:
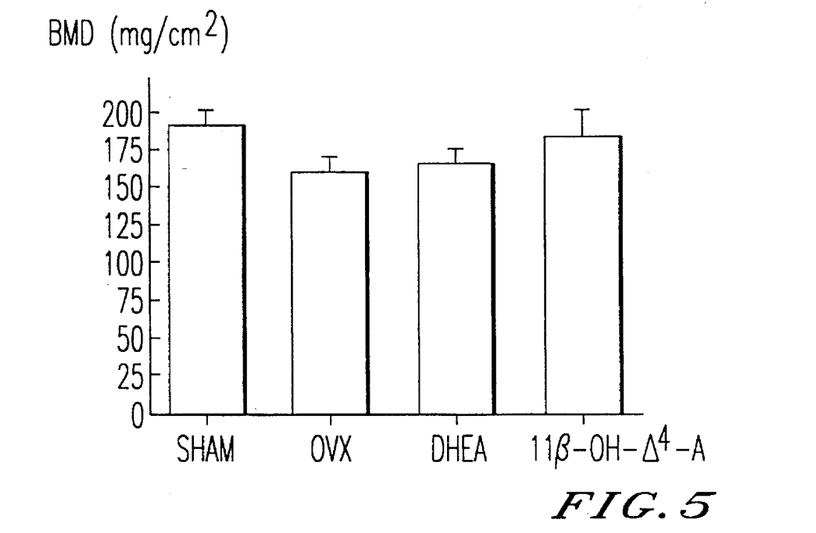
Figure 6:
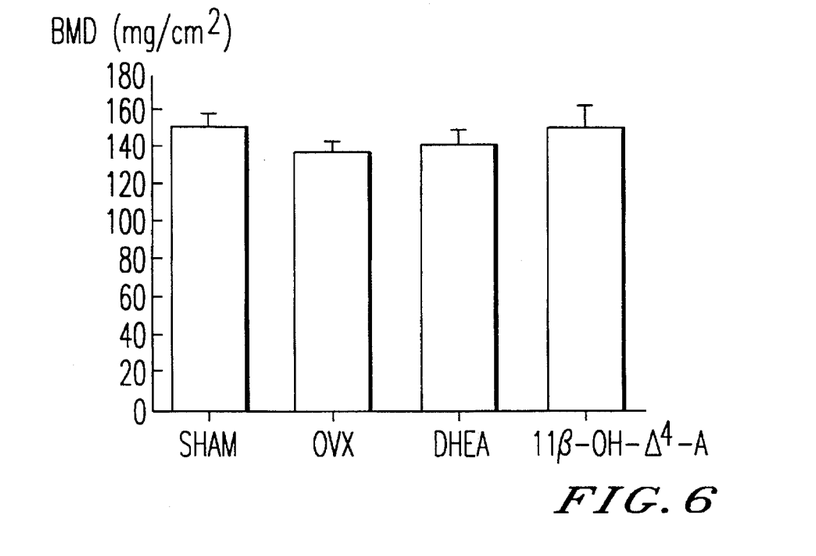

Improving Effects on the Osteogenesis Depression
in Postovariectomy Osteoporosis From a 7-weeks old female Wistar rat, the ovaria were both excised and three months after that, administration of a drug was started. As the drug, 11β-OH-$\Delta^4$-A, was administered dorsi-subcutaneously three times a week, each, at 0.1 mg/kg or 1 mg/kg. Subsequent to the administration of the drug for 1 month, the femurs and shinbones were collected. From the right femur and both the shinbones, osteoblasts were collected and the formation of colonies (FCFUs) of osteogenic precursor cells was observed. The results are shown in FIG. 2.

As is apparent from the graph, a significant drop in the FCFU forming ability was observed after the ovariectomy compared with that of a sham-operated group, which suggests reduced osteogenesis in the ovaryectomized group (OVX). In the group to which 11β-OH-$\Delta^4$-A was administered at 0.1 mg/kg, on the other hand, a marked increase in the FCFU formation was observed. From these results, it has become clear that the administration of 11β-OH-$\Delta^4$-A even in an amount as small as 0.1 mg/kg thrice a week for a month successfully normalized back the osteogenesis depression observed after the ovariectomy. As will be described subsequently herein, the sex hormone action of 11β-OH-$^4$-A in such a small amount is considered to be very weak.

TEST 5

Improving Effects on the Bone Mass Reduction in
Postovariectomy Osteoporosis

From a 7-weeks old female Wistar rat, the ovaria were both excised. Three months after that, the administration of a drug was started. As the drug, 11β-OH-$^4$-A or dihydroepiandrosterone (DHEA) was dorsisubcutaneously administered three times a week, each, at 1 mg/kg. After the drug administration was continued for 3 months, the femurs and shinbones were collected and the bone-salt amount was measured at three places, that is, the proximal end, diaphysis and distal end. The measurements of the bone-salt amount were conducted using an Aloka DCS-600 model by dual energy X-ray absorptiometry (DXA). The results are shown in FIGS. 3–6.

As is apparent from these graphs, the bone-salt amount of the ovariectomized group (OVX) decreased at each of the places of the femur but by the administration of 11β-OH-$\Delta^4$-A, it recovered to similar levels to those of the Sham-operated rat at the places, respectively. The effects of the above invention compound was more potent than those of dihydroepiandrosterone which has already been reported to have bone-salt improving effects on the ovariectomized rat.

Figure 7:
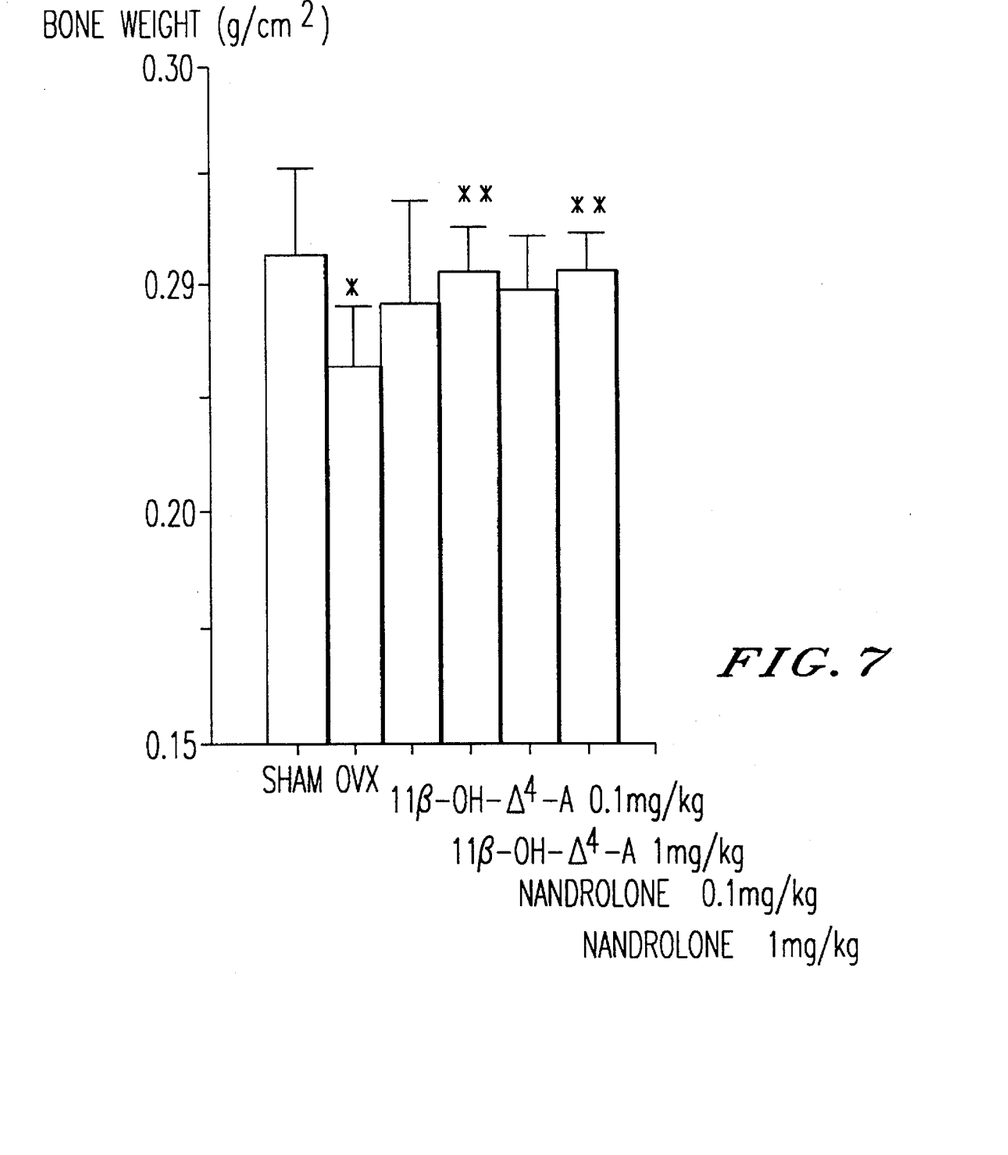
FIG. 7 illustrates bone-salt increasing effects of the invention compounds at the femoral proximoepiphysis.

The results similarly obtained in comparison with nandrolone are shown in FIG. 7.

From the results, 11β-OH-Δ⁴-A has been found to have similar bone-salt increasing effects on the proximal end of the femur to nandrolone.

TEST 6

Androgenic Action and Anabolic Action (1) In accordance with the Hershberge method, a castrated, 4-weeks old, Wistar, male rat (6 rats per group) was subcutaneously administered with 11-OH-Δ⁴-A at 0.1–0.3 mg/rat/day for 10 successive days. Similarly, a vehicle (sesame oil) was administered to the Sham-operated group and a control group, and testosterone propionate (T.P.) was administered at 0.1 mg/rat/day as a positive control. On the day following the completion of the administration, the anterior lobe of prostate and the musculus levator ani were excised and weighed. From a change in the weight of the anterior lobe of the prostate and the musculus levator ani, androgenic action and anabolic action were studied.

Figure 8:
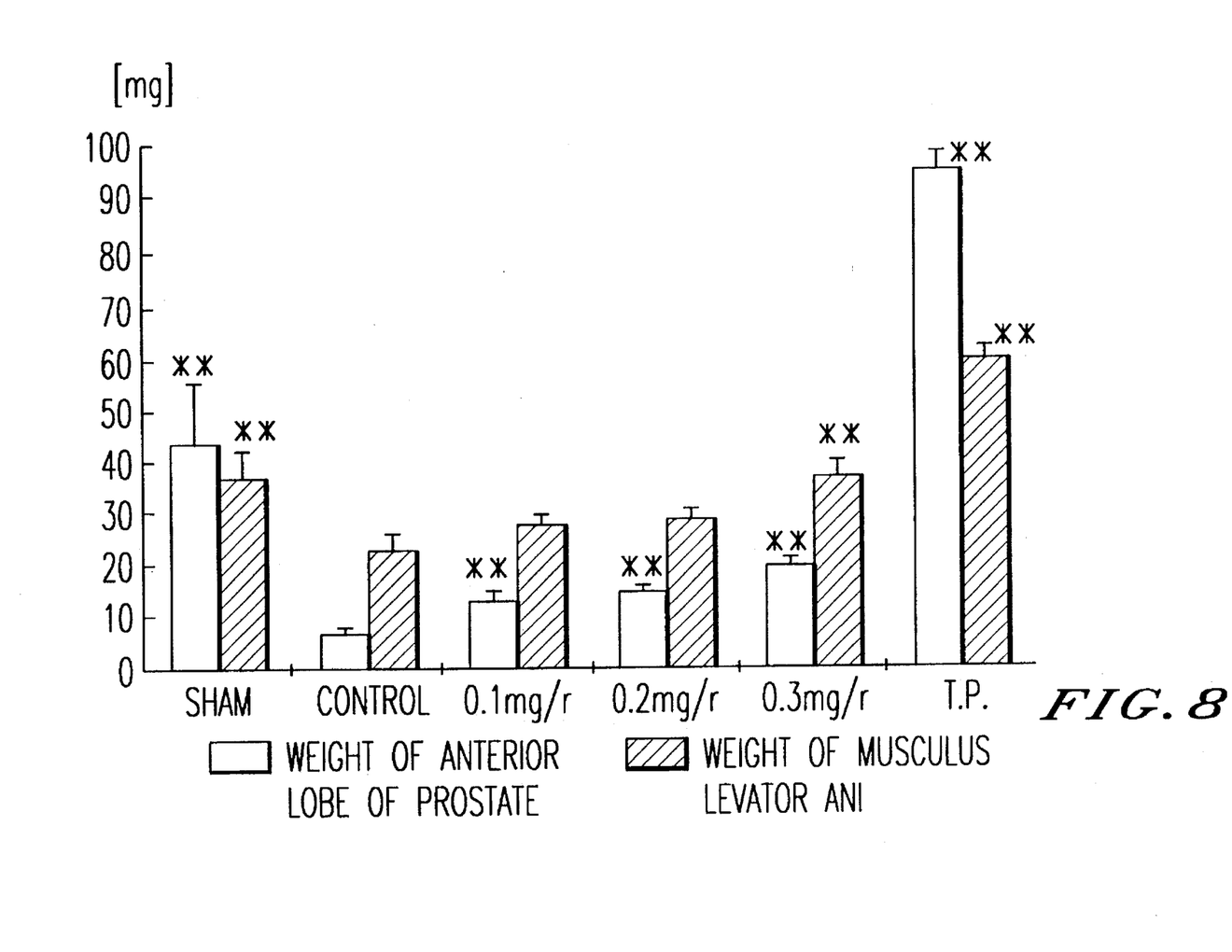
FIGS. 8–10 illustrate virilizing and protein assimilating effects of the invention compound.

The results are shown in FIG. 8.

The followings have been found from the results shown in the graph:

Androgenic action: 11β-OH-Δ⁴-A is considered to have androgenic action, because a significant increase in the weight of the prostate was observed when it was administered at 0.1–0.3 mg/rat/day (0.6–1.8 mg/kg/day). Its action was, however, very weak and compared with testosterone, the ratio was about 1:0.07.

Anabolic action: An increase in the weight of the musculus levator ani, which is an index of anabolic action, was observed in the administration of 11β-OH-Δ⁴-A at 0.3 mg/rat/day.

(2) In accordance with the Hershberge method, a 10 castrated, 4-weeks old, SD male rat (6 rats per group) was subcutaneously administered at 1 or 10 mg/kg/day for 7 successive days. Similarly, a vehicle (sesame oil) was administered to the Sham-operated group and a control group (Cestration); testosterone propionate was administered at 0.1 or 1 mg/kg/day as a positive control; and nandrolone was administered at 0.1, 1 or 10 mg/kg/day as a comparative compound.

Figure 9:
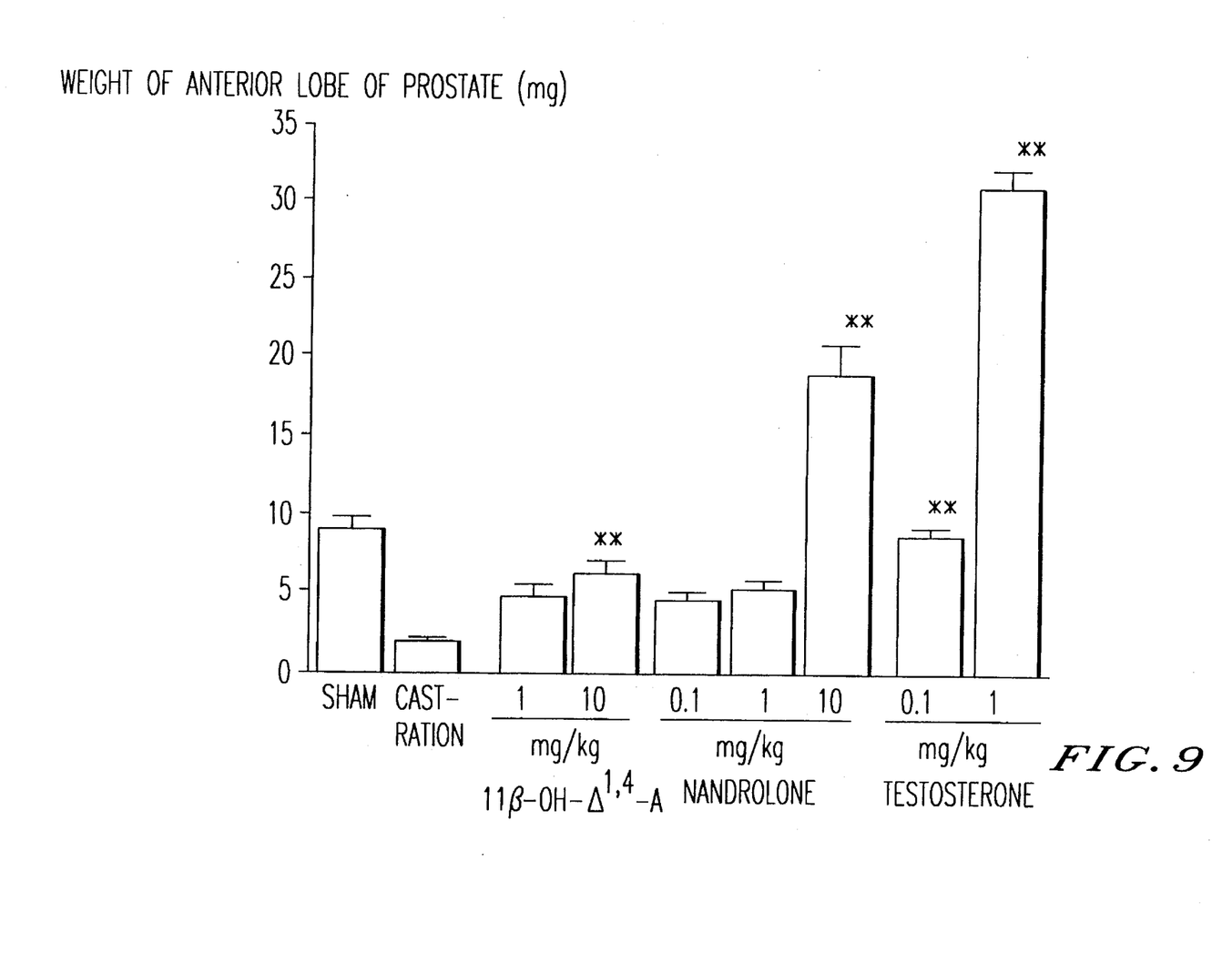
Figure 10:
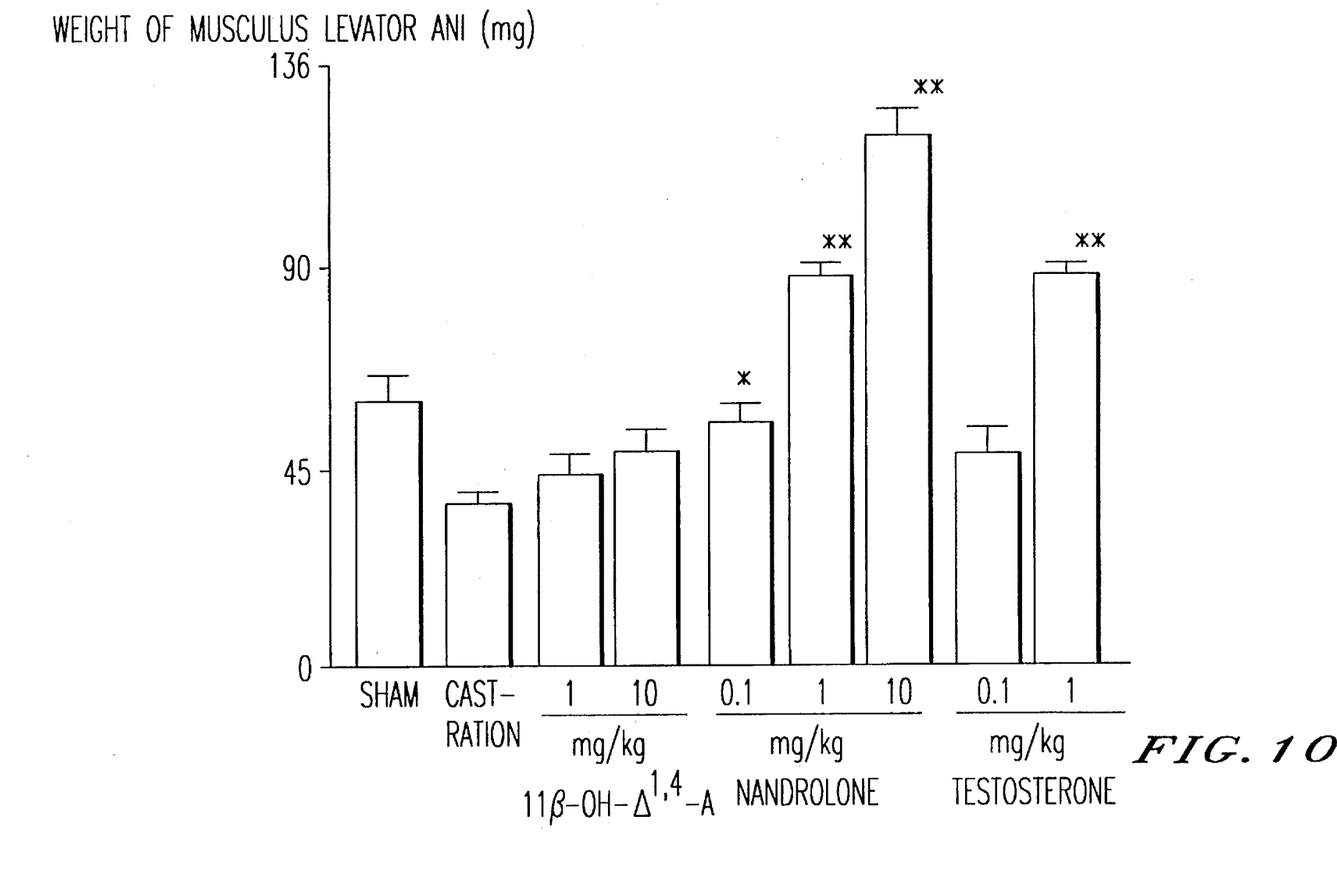

Androgenic action and anabolic action were studied in a manner similar to the above (1) and the results are shown in FIGS. 9 and 10.

Judging from the results, the invention compound has androgenic action and protein assimilating effects, though very weak.

Its androgenic action and anabolic action are extremely weak even compared with nandrolone or testosterone so that it has been found to be a drug free from danger of causing adverse effects when administered as a remedy for bone diseases.

TEST 7

Estrogenic Action (1) In accordance with the Louson method, a 21-days old Wistar female rat (6 rats per group) was subcutaneously administered with 11β-OH-Δ⁴-A at 0.1–3.0 mg/rat/day twice a day for 3 days. Similarly, a vehicle (sesame oil) was administered to a control group and estradiole benzoate was administered at 0.1 μg/rat/day as a positive control. On the day following the completion of the final administration, the uterus was excised. The estrogenic action was studied by weighing the uterus so excised.

Figure 11:
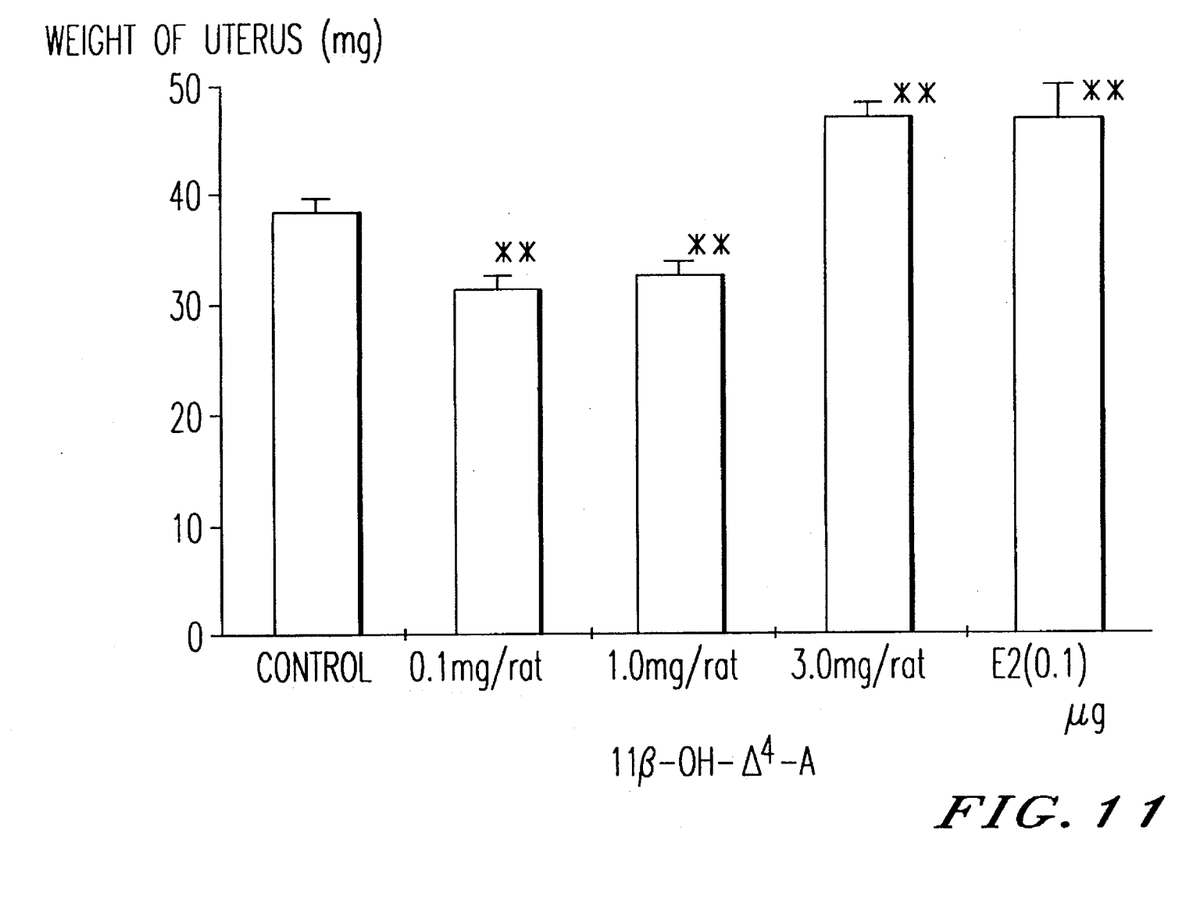
FIGS. 11–12 illustrate estrogenic action of the invention compound.

The results are shown in FIG. 11.

(2) From a 3-weeks old SD female rat, the ovaria were both excised. After the ovariectomized rat was fed for 11 days, it was subcutaneously administered with 11β-OH-Δ¹,⁴-A at 1 or 10 mg/kg/day for 3 successive days.

Similarly, a vehicle (sesame oil) was administered to a control group, 17β-estradiole was administered as a positive control and nandrolone was administered as a comparative compound. After the treatment in a similar manner to the above (1), the estrogenic action was studied.

Figure 12:
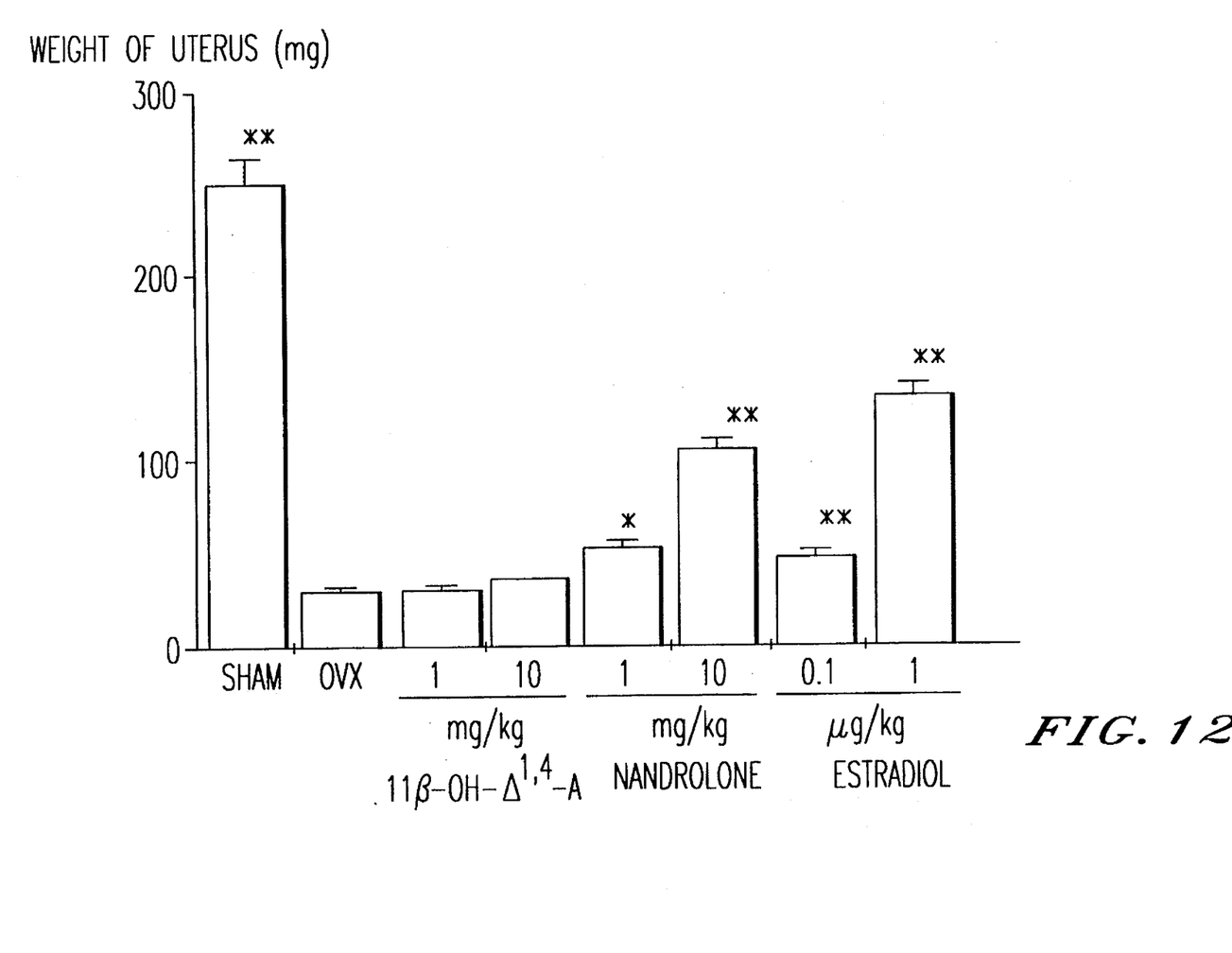

The results are shown in FIG. 12.

From the results, it was found that the invention compound hardly exhibited effects on the weight of the uterus, which is an index of estrogenic action, and showed only faint estrogenic action compared with estradiole or nandrolone.

TEST 8

Toxicity Test

An acute toxicity test of the invention compound 11β-OH-Δ⁴-A was conducted in the following manner.

To a Wistar rat, 11β-OH-Δ⁴-A was subcutaneously administered in an amount considered to be an intoxicating dose. The conditions of the rat were observed and at the same time, the $LD_{50}$ value was determined.

As the result, the $LD_{50}$ value of 11β-OH-Δ⁴-A was found to be 1000 mg/kg or greater.

As is apparent from the above test results, the invention compound has excellent osteogenesis promoting and bone-mass increasing effects but low adverse effects owing to weak androgenic action, protein assimilating effects and estrogenic action, so that it can be used for the remedies for calcium dysbolism and osteoporosis.

The invention compound can be administered, together with a conventionally used pharmaceutical vehicle, to humans as a pharmaceutical composition. Examples of the preparation form of such a pharmaceutical composition include preparations for oral administration such as tablets, capsules, powders, troches, liquid preparations and the like. It can also be administered as an injection. The preparations for oral administration can be formulated in a manner known to date. For example, the invention compound 11β-OH-Δ⁴-A, 11β-OH-Δ¹,⁴-A or the salt thereof can be formulated into tablets, capsules, powders, granules or the like by using in combination an excipient such as starch, mannitol or lactose; a binder such as carboxymethylcellulose sodium or hydroxypropylcellulose; a disintegrator such as crystalline cellulose or carboxymethylcellulose calcium; lubricant such as talc or magnesium stearate; and/or a fluidity improver such as light silicic anhydride, at need.

The dose of the osteogenesis promoter and/or osteoporosis remedy according to the present invention to human may vary depending on the age, symptoms and the like. Desired is, however, the administration at 0.1–10 mg/day, preferably 0.1–5 mg/day as an active ingredient of the androgen derivative (1) or the salt thereof in 1–3 portions.

EXAMPLES

The followings are formulation examples.

| Tablets Composition: | |
|---|---|
| Invention compound | 3 g |
| Lactose | 140 g |
| Crystalline cellulose | 26 g |
| Corn starch | 26 g |
| 3% Hydroxypropylcellulose | 100 ml |
| Magnesium stearate | 2 g |

Process: The invention compound, lactose, crystalline cellulose and corn starch were shifted through a 60-mesh sieve and mixed uniformly. The resulting uniform mixture was charged in a kneader, to which a 3% aqueous solution of hydroxypropylcellulose was poured and kneading was conducted. The mass so obtained was subjected to filtration and granulation through a 16-mesh die, followed by blow drying at 50° C. After the drying, the granules were sifted through a 16-mesh sieve, followed by mixing with magnesium stearate. The resulting mixture was compressed into tablets, each 200 mg in weight, by a tableting machine.

| Capsules Composition: | |
|---|---|
| Invention compound | 3 g |
| Lactose | 145 g |
| Corn starch | 50 g |
| Magnesium stearate | 2 g |

Process: The above ingredients were pulverized into powder, followed by stirring sufficient to obtain a uniform mixture. The resulting powder mixture was placed in gelatin capsules, in 0.2 g portions, to form capsules.

Capability of Exploitation in Industry

The osteogenesis promoter and/or osteoporosis remedy provided by the present invention is useful for the treatment of a morbid condition of osteogenesis depression such as osteogenesis depression caused by aging, immobilization or administration of a glucocortico, because its active ingredient, that is, the androgen derivative (1) or a salt thereof, particularly 11β-OH-Δ$^4$-A, 11β-OH-Δ$^{1,4}$-A or the salt thereof activates osteoblasts, promotes osteogenesis and increases the bone mass. It is also useful for the treatment of osteoporosis accompanying the above morbid condition and also osteoporosis after ovariectomy or menopause.

We claim:

1. An osteogenesis promoter and/or osteoporosis remedy comprising, as an active ingredient, an androgen derivative selected from the group consisting of 11β-hydroxyandrostane-3,17-dione, 11β-hydroxy-1-androstene-3,17-dione, and 11β-hydroxy-1,4-androstadiene-3,17-dione; or a salt thereof.

2. An osteogenesis promoter and/or osteoporosis remedy according to claim 1 wherein the androgen derivative is 11β-hydroxy-1,4-androstadiene-3,17-dione.

3. An osteogenesis promoter and/or osteoporosis remedy composition, comprising an androgen derivative represented by the following formula (1):

wherein each broken line indicates that the relevant carbon-to-carbon bond is a single bond or a double bond or a salt thereof; and a pharmaceutical vehicle.

4. The composition of claim 3 wherein the androgen derivative is selected from the group consisting of 11β-hydroxy-4-androstene-3,17-dione and 11β-hydroxy-1,4-androstadiene-3,17-dione.

5. A method for the remedial treatment of osteodysbolism and/or osteoporosis, which comprises administering, to a patient suffering from osteodysbolism and/or osteoporosis, an effective amount of an androgen derivative represented by the following formula (1):

wherein each broken line indicates that the relevant carbon-to-carbon bond is a single bond or a double bond; or a salt thereof.

6. The method of claim 5 wherein the androgen derivative is selected from the group consisting of 11β-hydroxy-4-androstene-3,17-dione and 11β-hydroxy-1,4-androstadiene-3,17-dione.

* * * * *